US012121397B2

(12) United States Patent
Meurer et al.

(10) Patent No.: US 12,121,397 B2
(45) Date of Patent: Oct. 22, 2024

(54) SYSTEMS AND METHODS FOR PASSIVE WIRE MANAGEMENT

(71) Applicant: General Electric Company, Schenectady, NY (US)

(72) Inventors: Robert Andrew Meurer, Waukesha, WI (US); Philip Stankard, Waukesha, WI (US); Craig Robert Loomis, Wauwatosa, WI (US); Allison Nicole Garza, Waukesha, WI (US); Ross Stalter, Waukesha, WI (US); Naum Muchnik, Yokneam Illit (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 811 days.

(21) Appl. No.: 16/550,894

(22) Filed: Aug. 26, 2019

(65) Prior Publication Data
US 2019/0374197 A1    Dec. 12, 2019

Related U.S. Application Data

(63) Continuation of application No. 15/087,466, filed on Mar. 31, 2016, now abandoned.

(51) Int. Cl.
*A61B 8/00* (2006.01)
*H02G 11/00* (2006.01)

(52) U.S. Cl.
CPC .......... *A61B 8/4405* (2013.01); *A61B 8/4433* (2013.01); *A61B 8/462* (2013.01); *A61B 8/54* (2013.01); *H02G 11/003* (2013.01)

(58) Field of Classification Search
None
See application file for complete search history.

(56) References Cited

U.S. PATENT DOCUMENTS

| | | | | |
|---|---|---|---|---|
| 6,629,927 B1* | 10/2003 | Mesaros | ................ | A61B 50/13 600/437 |
| 2004/0114313 A1* | 6/2004 | Mata | ...................... | H02G 11/02 600/301 |
| 2004/0179332 A1* | 9/2004 | Smith | ..................... | A61B 50/13 361/679.41 |
| 2008/0067317 A1* | 3/2008 | Altonji | ............... | F16M 11/2064 248/604 |
| 2008/0249406 A1* | 10/2008 | Naruse | ..................... | A61B 8/00 600/437 |
| 2008/0255455 A1* | 10/2008 | Sokulin | ................ | A61B 8/4209 600/459 |
| 2009/0091881 A1* | 4/2009 | Lee | ...................... | F16M 11/046 248/223.41 |

(Continued)

*Primary Examiner* — Katherine L Fernandez
*Assistant Examiner* — Farouk A Bruce
(74) *Attorney, Agent, or Firm* — Bookoff McAndrews, PLLC

(57) ABSTRACT

A system (e.g., an ultrasound imaging system) is provided. The system includes an ultrasound probe having a cable, and an ultrasound probe holder configured to receive the ultrasound probe. The system further includes a housing supported by a base. The housing includes a connector port and a cable manage passage. The cable manage passage positioned at an upper end of the housing distal to the base. The cable extending through the cable manage passage and is attached to the connector port. The ultrasound probe holder is coupled to a front side of the housing.

22 Claims, 6 Drawing Sheets

(56) References Cited

U.S. PATENT DOCUMENTS

| | | | |
|---|---|---|---|
| 2010/0174185 A1* | 7/2010 | Wang | A61B 8/0841 |
| | | | 600/562 |
| 2010/0269603 A1* | 10/2010 | Shim | A61B 8/00 |
| | | | 73/866.5 |
| 2014/0192323 A1* | 7/2014 | Kakuma | A61B 5/0066 |
| | | | 351/246 |
| 2017/0235903 A1* | 8/2017 | McLaughlin | G01S 7/52084 |
| | | | 715/708 |

* cited by examiner

SYSTEMS AND METHODS FOR PASSIVE WIRE MANAGEMENT

CLAIMS OF PRIORITY

This application is a continuation (CON) of U.S. patent application Ser. No. 15/087,466 filed on Mar. 31, 2016. The above identified application is hereby incorporated herein by reference in its entirety.

FIELD OF THE INVENTION

Embodiments described herein generally relate to providing a method for passive wire management for a diagnostic medical imaging system.

BACKGROUND OF THE INVENTION

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging the volume or body).

Settings and/or configurations of the ultrasound system is controlled by a clinician using a user interface 110. FIG. 1 illustrates a perspective view of a conventional ultrasound system 100. In the conventional ultrasound systems 100, the user interface 110 is divided into three distinct elements a flat screen or display 104, a separate touchscreen 106, and an operating panel 108 conventionally mounted to a base 102 positioned below the operating panel 108. For example, the flat screen 104 displays one or more ultrasound images acquired by the ultrasound system 100. Additionally, the flat screen 104 may include a graphical user interface (GUI) that is used in connection with the operating panel 108. The touchscreen 106 is used by the user or clinician to configure or adjust settings of one or more ultrasound probes 116. The operating panel 108 includes physical buttons and a trackball used to interface with the GUI of the flat screen display 104.

The conventional ultrasound system 100 includes a probe holder 112 positioned at opposing adjacent sides of the operating panel 108. The probe holder 112 is configured to hold the ultrasound probes 116. The ultrasound probes 116 are coupled to the base 102 by a wire or cable 114. During movement of the conventional ultrasound system 100, the cable 114 can be tangled or dragged on the ground, caught in the wheels of the base 102, and/or the like potentially damaging the cable 114. Additionally, when the cable 114 is caught one or more of the ultrasound probes 116 may be dislodged from the probe holder 112, damaged, and/or the like. For these and other reasons, an improved wire management is needed for diagnostic medical imaging.

BRIEF DESCRIPTION OF THE INVENTION

In an embodiment a system (e.g., an ultrasound imaging system) is provided. The system includes an ultrasound probe having a cable, and an ultrasound probe holder configured to receive the ultrasound probe. The system further includes a housing supported by a base. The housing includes a connector port and a cable manage passage. The cable manage passage positioned at an upper end of the housing distal to the base. The cable extending through the cable manage passage, and is attached to the connector port. The ultrasound probe holder is coupled to a front side of the housing.

In an embodiment a housing is provided an ultrasound imaging system. The housing includes an arm mount coupled to a front side of the housing. The arm mount is configured to traverse along a vertical track of the housing. The arm mount is further configured to adjust at least one of a rotational position, a tilt angle, or a vertical position of a display. The housing includes a connector port coupled to a back side of the housing. The housing further includes a base and a cable manage passage positioned at opposing ends of the housing. The cable manage passage extending along two orthogonal directions of the housing. The cable manage passage including an entry aperture along a first orthogonal direction, and an exiting aperture along a second orthogonal direction. The connector port is positioned proximate to the exiting aperture.

In an embodiment a method (e.g., for manufacturing a housing for an ultrasound imaging system) is provided. The method includes providing a cover segment and a base. The cover segment includes a cable manage passage extending along two orthogonal directions. The cable manage passage includes an entry aperture along a first orthogonal direction and an exiting aperture along a second orthogonal direction. The method further includes defining a distance between the cover segment and the base based on a length of a cable of an ultrasound probe.

DETAILED DESCRIPTION OF THE INVENTION

Figure 1:
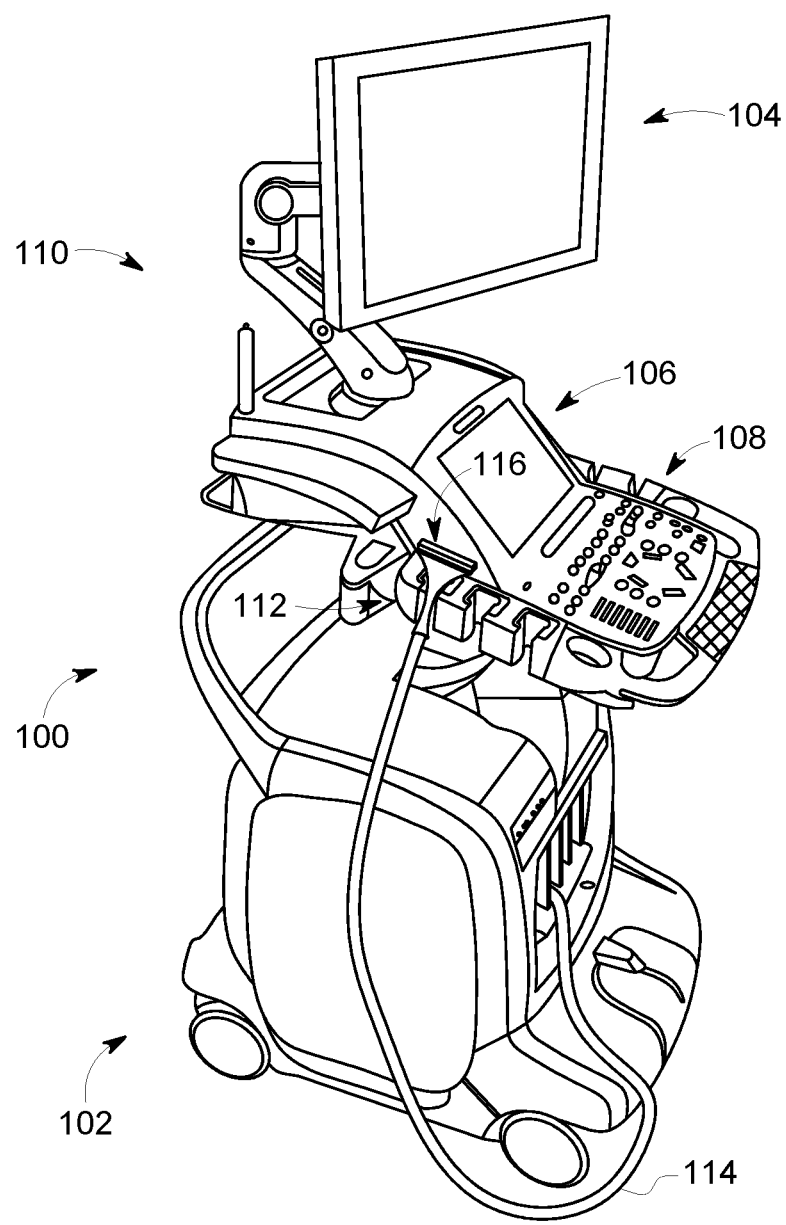
FIG. 1 illustrates a perspective view of a conventional ultrasound system.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods to passively manage cords, cables, and/or wires of a diagnostic medical imaging system, such as an ultrasound imaging system. Embodiments described herein positions ultrasound probes and/or connectors at an elevated position of the ultrasound imaging system. Based on the position of the ultrasound probes and/or connectors, cables will remain off the floor preventing possible damage to the ultrasound probes reducing costs (e.g., replacement ultrasound probes can range from $3,000-5,000) and/or maintaining patient scheduling throughput, and contained within a proximity envelope of the ultrasound imaging system. For example, a housing of the ultrasound imaging system is designed to position the ultrasound probes and connectors at a high position relative to the housing. Additionally, a column shape of the housing provides a thermally efficient form relative to conventional housings.

Figure 2:
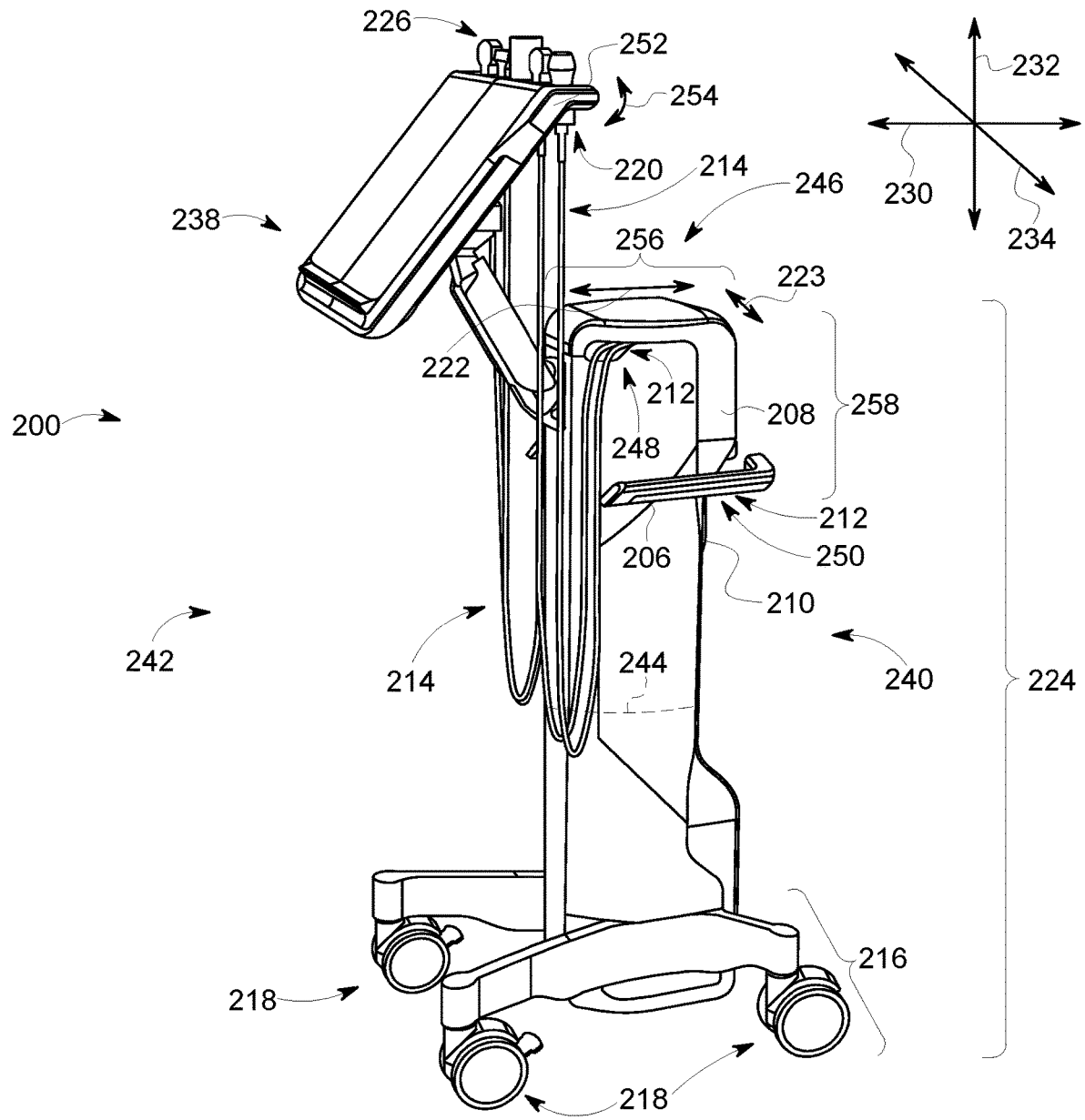
FIG. 2 illustrates a perspective view of an ultrasound imaging system, in accordance with an embodiment.

FIG. 2 illustrates a perspective view of an ultrasound imaging system 200, in accordance with an embodiment. The ultrasound imaging system 200 includes a housing 202, a display 238, and one or more ultrasound probes 226. The housing 202 has a column shape extending from a base 216 to a cover segment 208 defining a height 224 of the housing 202. The height 224 extends along a longitudinal axis 232. The housing 202 may have a substantially rectangular form. For example, the housing 202 may have two orthogonal sides corresponding to a width 223 and a length 222. Optionally, the sides of the housing 202 may be curved such that the sides are non-orthogonal with respect to each other. The width 223 may extend along an axis 234, and the length 222 may extend along an axis 230. The height 224 of the housing 202 is greater than the width 223 and/or the length 222. For example, a distance of the height 224 extending along the longitudinal axis 232 is greater than distances of the width 223 and the length 222 extending along the axes 234 and 230, respectively. In another example, a length of the height 224 along the longitudinal axis 232 may be a first magnitude greater than a length of the width 223 along the axis 234, and the length of the height 224 may be a second magnitude greater than a length of the of the length 222 along the axis 230.

The base 216 is configured to support the housing 202 and/or the ultrasound imaging system 200. Optionally, the base 216 may include a plurality of wheels 218 enabling the base 216 and the housing 202 to be mobile, such as movable base. For example, the base 216 may change positions or locations within a room, be moved to an alternative room or building relative to a prior location of the base 216, and/or the like. Additionally or alternatively, the housing 202 may be extended to form a stationary base, which does not include the plurality of wheels 218. For example, the housing 202 may be mounted to a wall of the room, mounted to a bed of the patient, does, and/or the like.

Optionally, the housing 202 may include one or more handles 206 extending from the housing 202. The handle 206 may extend along one or more sides of the housing 202. For example, the handle 206 may extend along a lateral side and a back side 240 of the housing 202. In operation, the handle 206 may be utilized by the user to adjust a position of the ultrasound imaging system 200.

The housing 202 may include a connector port 210. The connector port 210 may be positioned along the back side 240 of the housing 202. Optionally, the connector port 210 may be positioned on a lateral side of the housing 202 extending along the axis 234. Additionally or alternatively, the connector port 210 may be positioned more proximate to the cover segment 208 relative to the base 216 of the housing. For example, the connector port 210 is positioned between the cover segment 208 and a mid-point 244 that is positioned at half the height 224 of the housing 202.

The connector port 210 may be configured to attach one or more of the ultrasound probes 226 to the housing 202. For example, each of the ultrasound probes 226 include a cable 214 extending from the ultrasound probe 226. The connector port 210 is configured to be coupled to the one or more cables 214, thereby attaching the one or more cables 214 to the housing 202. The connector port 210 may be attached externally to the housing 202. For example, the connector port 210 is configured to be accessible from outside the housing 202. Additionally or alternatively, the connector port 210 may be built into and/or disposed on an external surface of the housing 202. For example, the one or more cables 214 can be operably attached to the connector port 210 without having to run the one or more cables 214 inside the housing 202. The connector port 210 further electrically couples one or more of the ultrasound probes 226 to one or more components within the housing 202. For example, when the one or more cables 214 is coupled to the connector port 210 the ultrasound probe 226 may be electrically coupled to a controller circuit (e.g., a controller circuit 626 in FIG. 6), such that the controller circuit 226 may receive ultrasound signals from the ultrasound probe 226. Optionally, the connector port 210 may include a flap, cover, removable plug insert, and/or the like for preventing an ingress of foreign contaminates into the connector port 210 when the one or more cables 214 is not operably attached to the connector port 210.

The cover segment 208 of the housing 202 is positioned opposite and/or distal from the base 216. Additionally or alternatively, the cover segment 208 may extend from a top 246 of the housing 202 to a side corresponding to a position of the connector port 210. For example, the cover segment 208 may extend from a front 242 to the back side 240 of the housing 202. Additionally or alternatively, a secondary storage container (not shown) may be positioned on top of the cover segment 208. For example, the secondary storage container may be configured to hold medical supplies (e.g., gloves, towels, gel, and/or the like), sterilization equipment (e.g., ultrasound probe sleeves, service wipes, and/or the like), and/or the like. The cover segment 208 further includes a cable manage passage 212.

The cable manage passage 212 is positioned an upper end of the housing 202 distal to the base 216. The cable manage passage 212 may be a cavity extending within the cover segment 208. Additionally or alternatively, the cable manage passage 212 may be channel extending along an outer surface of the cover segment 208. The cable manage passage 212 includes an entry aperture 248 and an exiting aperture 250. The entry aperture 248 may be positioned to face at the front 242 of the housing 202. Additionally or alternatively, the cable manage passage 212 may include one or more entry apertures 248 positioned to face a lateral side(s) and/or the front 242 of the housing 202. For example, the cable manage passage 212 may include a first entry aperture and a second entry aperture positioned at opposing lateral sides of the housing 202. The first and second entry apertures are configured to receive a portion of the one or more cables 214. For example, the first entry aperture may receive a first set of the cables 214, and the second entry aperture may receive a second set of the cables 214.

The exiting aperture 250 may be positioned at the back side 240 of the housing 202 proximate to the connector port 210. The cable manage passage 212 may extend along two orthogonal directions of the housing 202 and/or cover segment 208. For example, a first portion 256 of the cable manage passage 212 may extend from the entry aperture 230 aligned with the axis 230 along the housing 202. A second portion 258 of the cable manage passage 212 may extend along the axis 232 terminating at the exiting aperture 250 toward the connector port 210.

The cable manage passage 212 may be configured to direct the one or more cables 214 from the front 242 of the housing 202 to the connector port 210. For example, the one or more cables 214 traverse within the cable manage passage 212 extending from the entry aperture 248 to the exiting aperture 250 proximate to the connector port 210. Optionally, the cable manage passage 212 may guide the one or more cables 214 along different directions (e.g., two orthogonal directions) of the housing 202. For example, the cable manage passage 212 may direct the one or more cables 214 from the entry aperture 248 along the axis 230 and direct the one or more cables 214 to the exit aperture 250 along the axis 232 orthogonal to the axis 230. It may be noted based on the cable manage passage 212 the housing 202 produces a gap between the one or more ultrasound probes 226 and the connector port 210. For example, since the one or more cables 214 extend through the cable manage passage 212 of the cover segment 208 the housing 202 is continually interposed between the one or more ultrasound probes 226 and the connector port 210 along the axis 230.

The display 238 is coupled to the front side 242 of the housing 202. The display 238 may be a crystal display (e.g., light emitting diode (LED) backlight), organic light emitting diode (OLED) display, plasma display, CRT display, and/or the like. The display 238 may be a touch screen display. For example, the display 238 may display a graphical user interface (GUI), which may be used by a user to control operations of the ultrasound imaging system 200.

The display 238 includes an ultrasound probe holder 220. The ultrasound probe holder 220 is configured to secure the one or more ultrasound probes 226 allowing the one or more cables 214 to dangle or hang freely from the one or more ultrasound probes 226. For example, the ultrasound probe holder 220 receives the one or more ultrasound probes 226 to maintain a position of the one or more ultrasound probes 226 with respect to the housing 202. The ultrasound probe holder 220 may be positioned along an edge of the display 238 proximate to the housing 202. For example, the ultrasound probe holder 220 may be interposed between the display 238 and the housing 202. Optionally, a position of the ultrasound probe holder 220 may be adjusted along a direction of an arrow 254 about a pivot point 252. In connection with FIG. 3, the one or more ultrasound probes 226 may be received by the ultrasound probe holder 220 into a respective slot 302.

Figure 3:
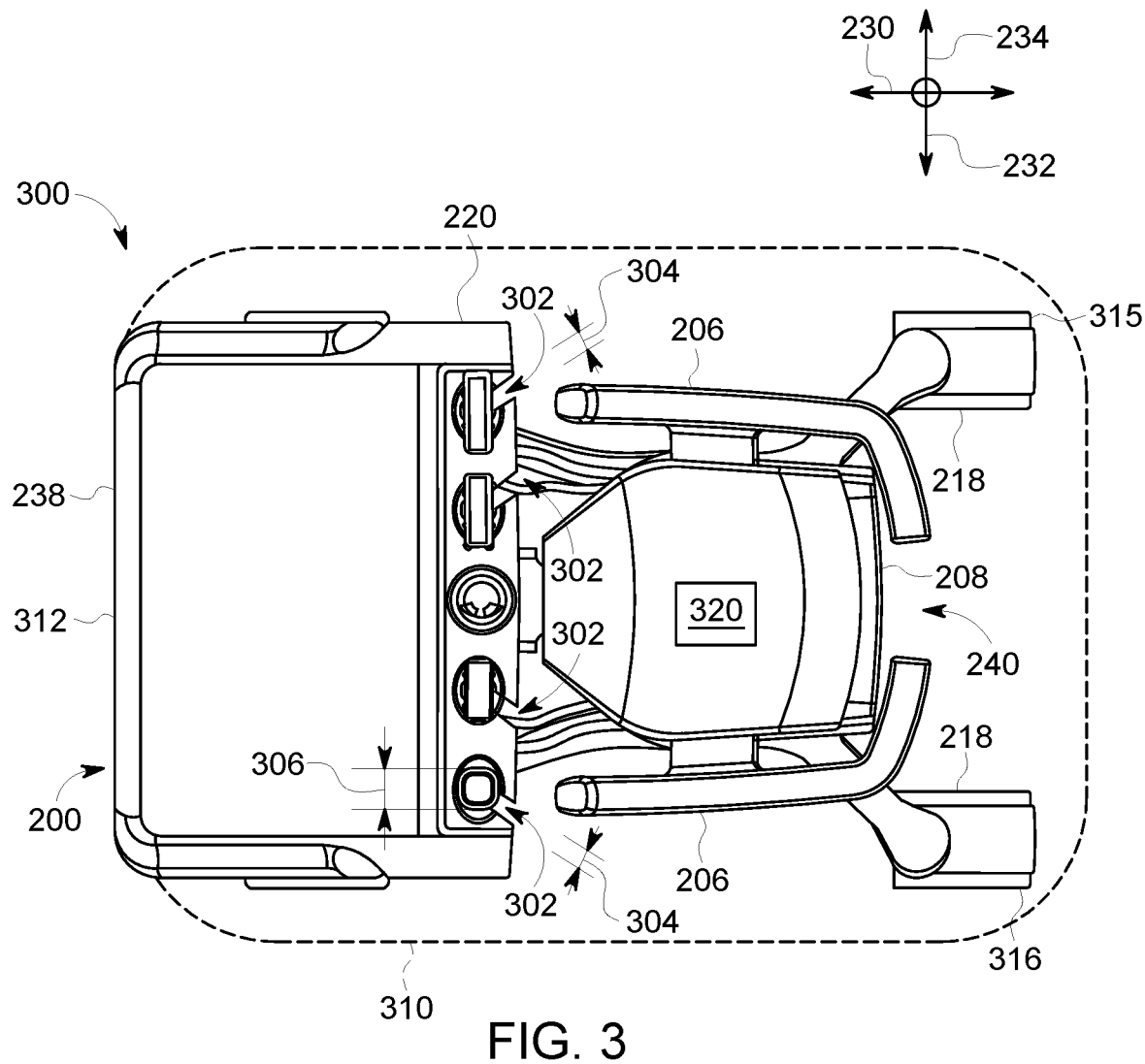
FIG. 3 illustrates a top view of the ultrasound imaging system shown in FIG. 2

FIG. 3 illustrates a top view 300 of the ultrasound imaging system 200. The ultrasound probe holder 220 includes a plurality of slots 302. Each of the slots 302 may have an entry diameter 304 and a resting diameter 306. The entry diameter 304 may be smaller than the resting diameter 306. The entry diameter 304 may be configured to allow a portion of the one or more ultrasound probes 226 and/or the one or more cables 214 to move into the resting diameter 306. The resting diameter 306 may be configured to be smaller than a portion of the one or more ultrasound probes 226. For example, the resting diameter 306 may be smaller than transducer heads of the one or more ultrasound probe 226.

Additionally or alternatively, the housing 202 may be configured to contain and/or maintain a position of the one or more ultrasound probes 226 and/or the one or more cables 214 within a footprint 310 of the ultrasound imaging system 200. For example, the cable manage passage 212 of the cover segment 208 and/or the ultrasound probe holder 220 may confine the one or more ultrasound probes 226 and/or the one or more cables 214 within the footprint 310. The footprint 310 may correspond to a proximity envelope of the ultrasound imaging system 200 defined by the housing 202. In various embodiments, a boundary of the footprint 310 may be defined by distal edges 312-318 of one or more components of the housing 202, the back side 240, and/or the like. For example, the boundary of the footprint 310 may be define by the distal edge 312 of the display 238, the distal edges 315-316 of the wheels 218, and/or the back side 240.

Optionally, on a top of the cover segment 208 may include one or more vents 320 proximate to the cable manage passage 212. Additionally or alternatively, the one or more vents 320 may be positioned along the back side 240 of the cover segment 208, a lateral side of the housing proximate to the cover segment 208, and/or the like. The vent 320 may correspond to a plurality of apertures or openings of the housing 202. The vent 320 may be configured to regulate a temperature within the housing 202. For example, the heated air may traverse from within the housing 202 and be exhausted from the vent 320 into the ambient air proximate to the cover segment 208 and/or external to the housing 202.

In various embodiments, an opposing vent proximate to the base 216 of the housing 202 may form a passive cooling system within the housing 202. The opposing vent may be facing a lateral side of the housing 202 along the axis 234, facing a distal end of the housing 202 toward the ground along the axis 232, facing the front 242 of the housing 202, and/or the like. The vent 320 and the opposing vent may enable air infiltration within the housing 202 generating a stack effect (e.g., chimney effect) within the housing 202. The vent 320 and the opposing vent may reduce a thermal temperature of one or more components within the housing 202. In operation, air within the housing 202 may absorb thermal energy generated by the components within the housing 202 to form heated air. The heated air may have a greater temperature than the ambient air external to the housing 202. The difference in air temperature creates a buoyancy force of the heated air within the housing 202. The buoyancy force propels the heated air within the housing 202 to the vent 320 allowing ambient air (having a lower temperature than the heated air) to enter the housing 202 via the opposing vent circulating air within the housing 202. The circulating air may reduce a temperature of the components within the housing 202.

Additionally or alternatively, the vent 320 and the opposing vent may be positioned at opposing ends of a channel (not shown) extending within the housing 202. For example, the channel may correspond to a conduit or passage within the housing 202 extending from the opposing vent to the vent 320. The channel may be configured to allow air flow to traverse within the channel from the opposing vent and the vent 320. Optionally, the channel may include one or more apertures extending from the channel to one or more components within the housing 202. For example, the one or more apertures may be configured to deliver ambient air traversing within the channel from the opposing vent to the one or more components.

Figure 4:
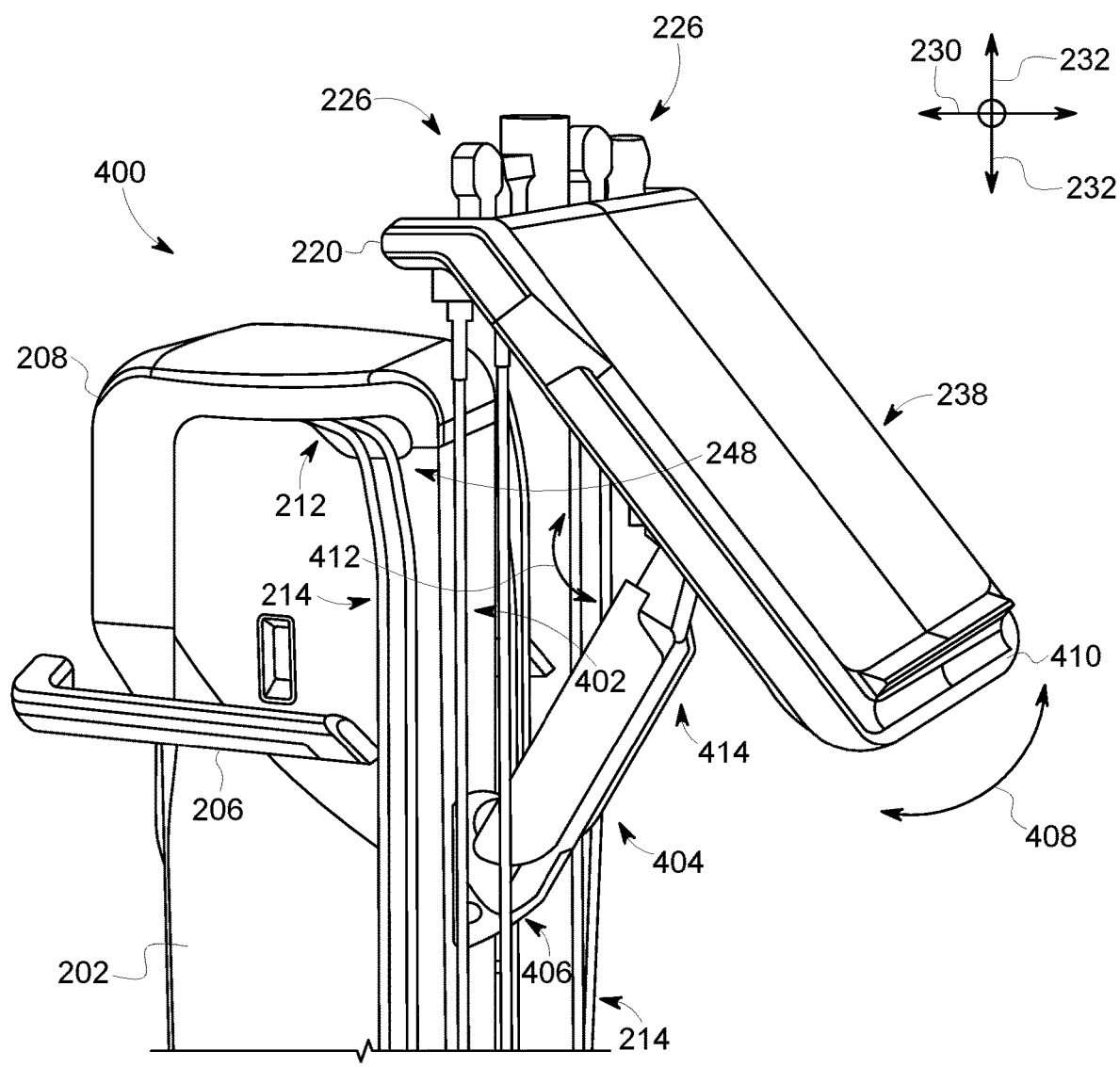
FIG. 4 illustrates a lateral view of a portion of the ultrasound imaging system shown in FIG. 2, in accordance with an embodiment.

FIG. 4 illustrates a lateral view 400 of a portion of the ultrasound imaging system 200, in accordance with an embodiment. The lateral view 400 shows an arm mount 404 extending from the front 242 of the housing 202. The arm mount 404 may be coupled to the housing 202 via a vertical track 402. The display 238 may be coupled and/or mounted to the arm mount 404. Optionally, the arm mount 404 may include one or more pivot joints 406 and 414 positioned at opposing ends of the arm mount 404. The one or more pivot joints 406 and 414 may be configured to adjust a rotational position of the arm mount 404 with respect to the housing 202, the display 238 with respect to the arm mount 404 and/or housing 202, and/or the like.

For example, the arm mount 404 may be coupled or mounted to the vertical track 402 of the housing 202 at the pivot joint 406. The pivot joint 406 may be configured to adjust a rotational position of the arm mount 404 (about a pivot point of the pivot joint 406) along a rotational arrow 408. In another example, the display 238 may be coupled or mounted to the arm mount 404 at the pivot joint 414. A tilt angle 412 of the display 238 may be adjusted using the pivot joint 414 of the arm mount 404 by rotating the display 238 about a pivot point of the pivot joint 414. Additionally or alternatively, the display 238 may include a position handle 410 extending from a distal end of the display 238. The position handle 410 may be utilized by the user to adjust the tile angle 412 and/or the rotational position of the monitor 248 with respect to the housing 202.

Additionally or alternatively, the arm mount 404 may be configured to guide the one or more cables 214 between the housing 202 and the probe holder 220. For example, the arm mount 404 may include fasteners, channels, grooves, and/or the like to couple, grip, hold, and/or the like at least a portion of the one or more cables 214 to the arm mount 404. During rotation, articulation, and/or the like of the display 238 relative to the housing 202, the arm mount 404 may guide and/or reposition the one or more cables 214 to confine the one or more cable 214 within the foot print 310 (FIG. 3).

The vertical track 402 may extend along at least a portion of the front 242 of the housing 202 along the axis 232. For example, the vertical track 402 may be overlaid on a portion of the housing 202. The arm mount 404 may traverse along the vertical track 402 adjusting a position of the arm mount 404 with respect to the housing 202. In operation, the arm mount 404 adjusts a vertical position of the display 238 when traversing along the vertical track 402. For example, the user may grasp the position handle 410 to move the arm mount 404 along the vertical track 402 to adjust a vertical position of the display 238.

Figure 5:
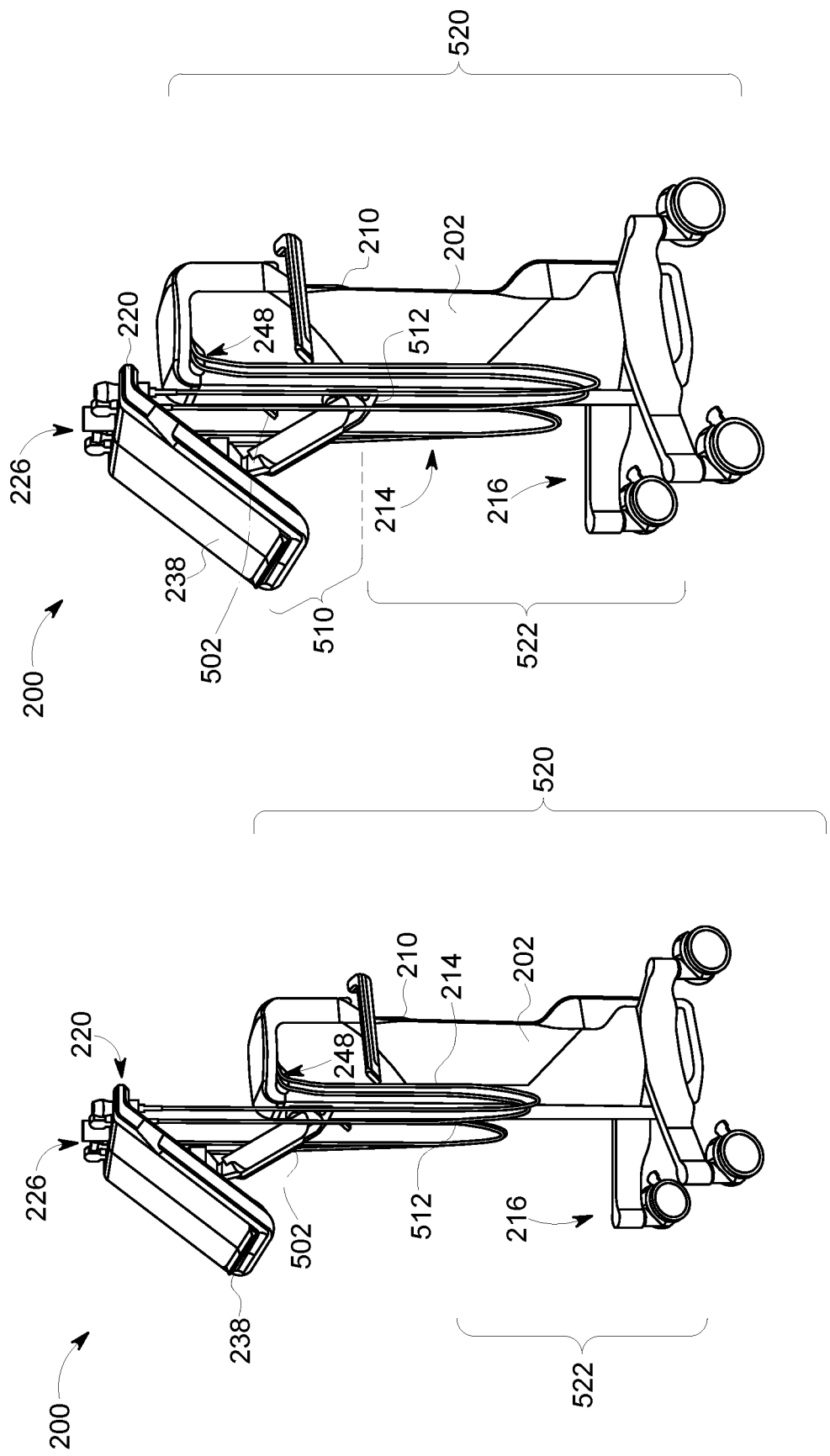
FIG. 5 illustrates a change in vertical position of a display of the ultrasound imaging system shown in FIG. 2

FIG. 5 illustrates a change in vertical position 510 of the display 238 of the ultrasound imaging system 200. For example, the display 238 is adjusted from a first vertical position 502 to a second vertical position 504. The second vertical position 504 is lower than and/or more proximate to the base 216 relative to the first vertical position 502. It may be noted that as the display 238 is lowered to the second vertical position 504, the ultrasound probes 226 secured in the ultrasound probe holder 220 are lowered concurrently with the display 238. As the ultrasound probes 226 are lowered, the one or more cables 214 hang freely from the ultrasound probes 226 but do not extend lower than the housing 202 and/or base 216. For example, the one or more cables 214 do not touch the ground when the display 238 is at the second vertical position 504.

In operation, a position of the cover segment 208 and/or a length of the vertical track 402 may be based on a length of the one or more cables 214 to prevent the one or more cables 214 to be in contact with the ground. For example, the cover segment 208 and/or the entry aperture 248 may be positioned at a height 520 of the housing 202 relative to the ground. The vertical track 402 may extend from a point 512 to the first vertical position 502. For example, the display 238 may be repositionable from the first vertical position 502 to the point 512. The point 512 corresponds to a position of the display 238 that is more proximate to the ground relative to other vertical positions of the display 238 along the vertical track 402. At the point 512, the display 238 may be positioned a height 522 from the ground. A sum of the heights 520 and 522 may be configured to be greater than a length of the one or more cables 214, which prevent the one or more cables 214 from being in contact with the ground.

Figure 6:
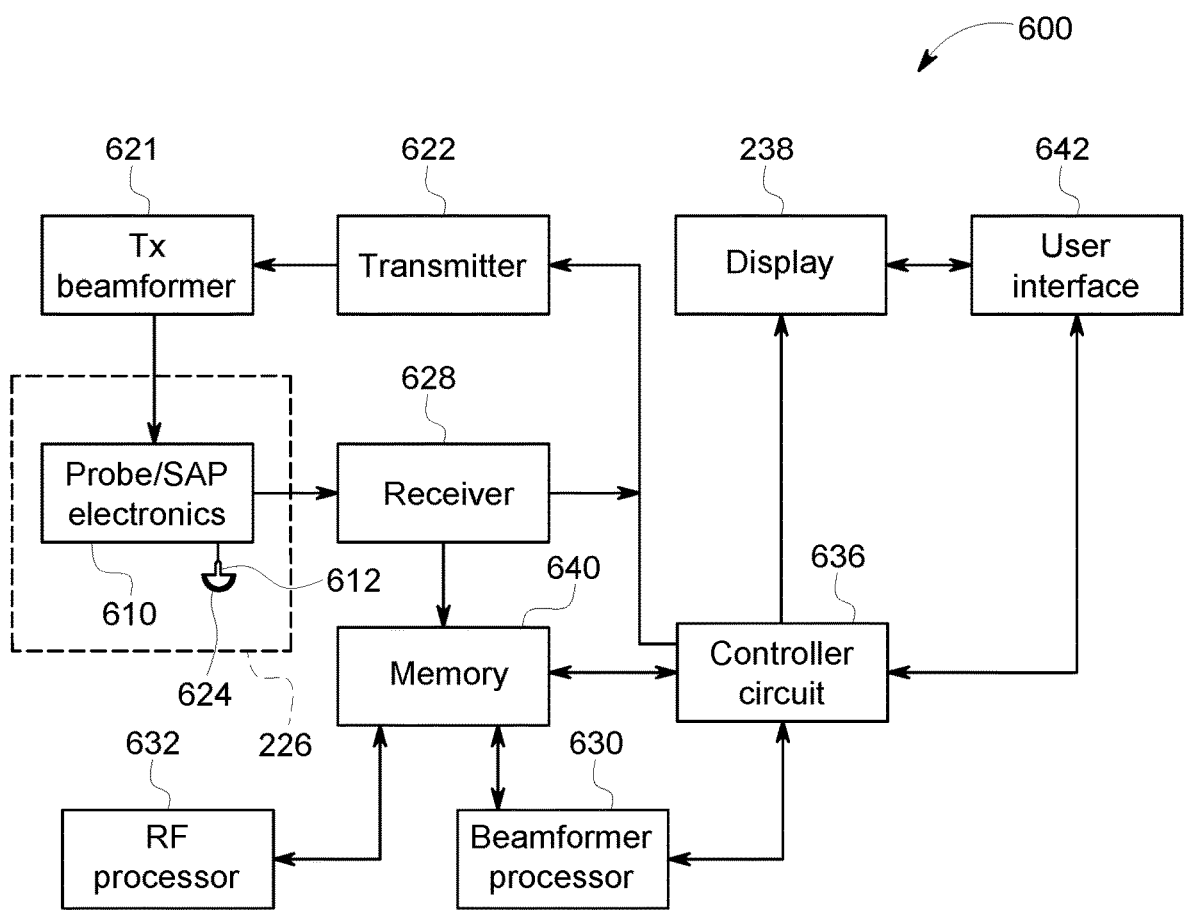
FIG. 6 is an illustration of a simplified block diagram of an ultrasound imaging system, in accordance with an embodiment.

FIG. 6 is a schematic diagram 600 of a diagnostic medical imaging system, specifically, the ultrasound imaging system 200. For example, the schematic diagram may illustrate one or more components that are within the housing 202. The ultrasound imaging system 200 includes one or more ultrasound probes 226, each having a transmitter 622 and probe/SAP electronics 610. Each of the ultrasound probes 226 may be configured to acquire ultrasound data or information from a region of interest (e.g., organ, blood vessel, heart) of the patient. The one or more ultrasound probes 226 are communicatively coupled to the controller circuit 636 via the transmitter 622. The transmitter 622 transmits a signal to a transmit beamformer 621 based on acquisition settings received by the user. The signal transmitted by the transmitter 622 in turn drives the transducer elements 624 within the transducer array 612. The transducer elements 624 emit pulsed ultrasonic signals into a patient (e.g., a body). A variety of a geometries and configurations may be used for the array 612. Further, the array 612 of transducer elements 624 may be provided as part of, for example, different types of ultrasound probes.

The acquisition settings may define an amplitude, pulse width, frequency, and/or the like of the ultrasonic pulses emitted by the transducer elements 624. The acquisition settings may be adjusted by the user by selecting a gain setting, power, time gain compensation (TGC), resolution, and/or the like from the user interface 642.

The transducer elements 624 emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from a region of interest (ROI) (e.g., heart, left ventricular outflow tract, breast tissues, liver tissues, cardiac tissues, prostate tissues, and the like) to produce echoes. The echoes are delayed in time and/or frequency according to a depth or movement, and are received by the transducer elements 624 within the transducer array 612. The ultrasonic signals may be used for imaging, for generating and/or tracking shear-waves, for measuring changes in position or velocity within the ROI (e.g., flow velocity, movement of blood cells), differences in compression displacement of the tissue (e.g., strain), and/or for therapy, among other uses. For example, the one or more probes 226 may deliver low energy pulses during imaging and tracking, medium to high energy pulses to generate shear-waves, and high energy pulses during therapy.

The transducer array 612 may have a variety of array geometries and configurations for the transducer elements 624 which may be provided as part of, for example, different types of the one or more ultrasound probes 226. The probe/SAP electronics 610 may be used to control the switching of the transducer elements 624. The probe/SAP electronics 610 may also be used to group the transducer elements 624 into one or more sub-apertures.

The transducer elements 624 convert the received echo signals into electrical signals which may be received by a receiver 628. The receiver 628 may include one or more amplifiers, an analog to digital converter (ADC), and/or the like. The receiver 628 may be configured to amplify the received echo signals after proper gain compensation and convert these received analog signals from each transducer element 624 to digitized signals sampled uniformly in time. The digitized signals representing the received echoes are stored on memory 640, temporarily. The digitized signals correspond to the backscattered waves receives by each transducer element 624 at various times. After digitization, the signals still may preserve the amplitude, frequency, phase information of the backscatter waves.

Optionally, the controller circuit 636 may retrieve the digitized signals stored in the memory 640 to prepare for the beamformer processor 630. For example, the controller circuit 636 may convert the digitized signals to baseband signals or compressing the digitized signals.

The beamformer processor 630 may include one or more processors. Optionally, the beamformer processor 630 may include a central controller circuit (CPU), one or more microprocessors, or any other electronic component capable of processing inputted data according to specific logical instructions. Additionally or alternatively, the beamformer processor 630 may execute instructions stored on a tangible and non-transitory computer readable medium (e.g., the memory 640) for beamforming calculations using any suitable beamforming method such as adaptive beamforming, synthetic transmit focus, aberration correction, synthetic aperture, clutter reduction and/or adaptive noise control, and/or the like.

The beamformer processor 630 may further perform filtering and decimation, such that only the digitized signals corresponding to relevant signal bandwidth is used, prior to beamforming of the digitized data. For example, the beamformer processor 630 may form packets of the digitized data based on scanning parameters corresponding to focal zones, expanding aperture, imaging mode (B-mode, color flow), and/or the like. The scanning parameters may define channels and time slots of the digitized data that may be beamformed, with the remaining channels or time slots of digitized data that may not be communicated for processing (e.g., discarded).

The beamformer processor 630 performs beamforming on the digitized signals and outputs a radio frequency (RF) signal. The RF signal is then provided to an RF processor 632 that processes the RF signal. The RF processor 632 may generate different ultrasound image data types, e.g. B-mode, color Doppler (velocity/power/variance), tissue Doppler (velocity), and Doppler energy, for multiple scan planes or different scanning patterns. For example, the RF processor 632 may generate tissue Doppler data for multi-scan planes. The RF processor 632 gathers the information (e.g. I/Q, B-mode, color Doppler, tissue Doppler, and Doppler energy information) related to multiple data slices and stores the data information, which may include time stamp and orientation/rotation information, in the memory 640.

Alternatively, the RF processor 632 may include a complex demodulator (not shown) that demodulates the RF signal to form IQ data pairs representative of the echo signals. The RF or IQ signal data may then be provided directly to the memory 640 for storage (e.g., temporary storage). Optionally, the output of the beamformer processor 630 may be passed directly to the controller circuit 636.

The controller circuit 636 may be configured to process the acquired ultrasound data (e.g., RF signal data or IQ data pairs) and prepare frames of ultrasound image data for display on the display 638. The controller circuit 636 may include one or more processors. Optionally, the controller circuit 636 may include a central controller circuit (CPU), one or more microprocessors, a graphics controller circuit (GPU), or any other electronic component capable of processing inputted data according to specific logical instructions. Having the controller circuit 636 that includes a GPU may be advantageous for computation-intensive operations, such as volume-rendering. Additionally or alternatively, the controller circuit 636 may execute instructions stored on a tangible and non-transitory computer readable medium (e.g., the memory 640).

The controller circuit 636 is configured to perform one or more processing operations according to a plurality of selectable ultrasound modalities on the acquired ultrasound data, adjust or define the ultrasonic pulses emitted from the transducer elements 624, adjust one or more image display settings of components (e.g., ultrasound images, interface components, positioning regions of interest) displayed on the display 638, and other operations as described herein. Acquired ultrasound data may be processed in real-time by the controller circuit 636 during a scanning or therapy session as the echo signals are received. Additionally or alternatively, the ultrasound data may be stored temporarily in the memory 640 during a scanning session and processed in less than real-time in a live or off-line operation.

The memory 640 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions (e.g., for the controller circuit 636, the beamformer processor 630, the RF processor 632), and/or the like. The memory 640 may be a tangible and non-transitory computer readable medium such as flash memory, RAM, ROM, EEPROM, and/or the like.

The memory 640 may store 3D ultrasound image data sets of the ultrasound data, where such 3D ultrasound image data sets are accessed to present 2D and 3D images. For example, a 3D ultrasound image data set may be mapped into the corresponding memory 640, as well as one or more reference planes. The processing of the ultrasound data, including the ultrasound image data sets, may be based in part on user inputs, for example, user selections received at the user interface 642.

The controller circuit 636 is operably coupled to the display 238 and a user interface 642. The display 238 may include one or more liquid crystal displays (e.g., light emitting diode (LED) backlight), organic light emitting diode (OLED) displays, plasma displays, CRT displays, and/or the like. The display 238 may display patient information, ultrasound images and/or videos, components of a display interface, one or more 2D, 3D, or 4D ultrasound image data sets from ultrasound data stored in the memory 640 or currently being acquired, measurements, diagnosis, treatment information, and/or the like received by the display 238 from the controller circuit 236.

The user interface 642 controls operations of the controller circuit 636 and is configured to receive inputs from the user. The user interface 642 may include a keyboard, a mouse, a touchpad, one or more physical buttons, and/or the like. Optionally, the display 238 may be a touch screen display, which includes at least a portion of the user interface 642.

For example, a portion of the user interface 642 may correspond to a graphical user interface (GUI) generated by the controller circuit 636 shown on the display 238. The GUI may include one or more interface components that may be selected, manipulated, and/or activated by the user operating the user interface 642 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

In various embodiments, the interface components may perform various functions when selected, such as measurement functions, editing functions, database access/search functions, diagnostic functions, controlling acquisition settings, and/or system settings for the ultrasound imaging system 200 performed by the controller circuit 636.

Figure 7:
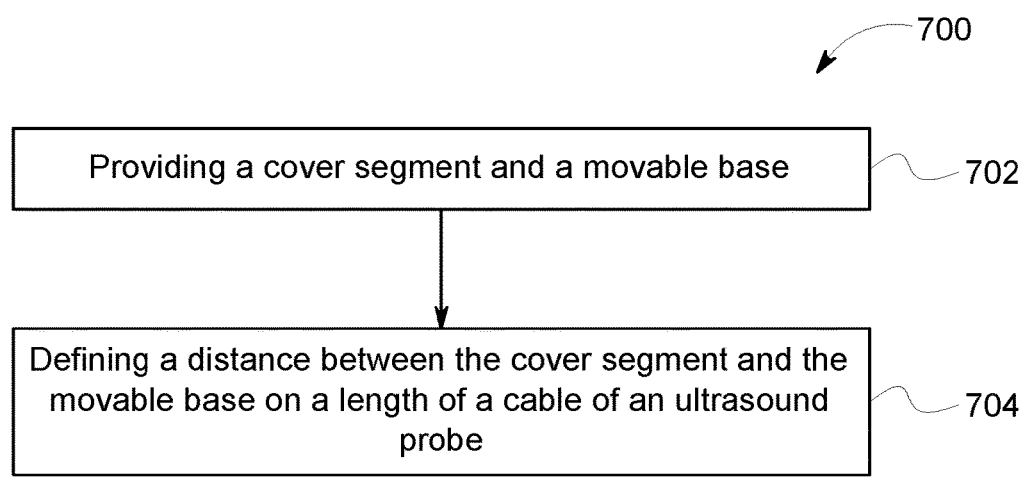
FIG. 7 illustrates a flow chart of a method in accordance with an embodiment.

FIG. 7 is a flow chart of a method 700 in accordance with an embodiment. The method 700 may be, for example, a method of manufacturing or assembling the housing 202 of the ultrasound imaging system 200. The method 700 may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

The method 700 includes providing, at 702, providing a cover segment and a base. The cover segment may be similar to and/or the same as, for example, the cover segment 208 (FIGS. 2-5). The cover segment includes a cable manage passage extending along two orthogonal directions. For example, the cable manage passage includes an entry aperture along a first orthogonal direction and an exiting aperture along a second orthogonal direction. The base may be similar to and/or the same as, for example, the cover segment 216 (FIGS. 2 and 5).

The method 700 also includes defining, at 704, a distance between the cover segment and the base based on a length of a cable (e.g., the one or more cables 214) of an ultrasound probe (e.g., the one or more ultrasound probes 226). For example, the distance may be configured to be greater than a length of the cable to prevent the cable 214 from being in contact with the ground.

In an embodiment a system (e.g., an ultrasound imaging system) is provided. The system includes an ultrasound probe having a cable, and an ultrasound probe holder configured to receive the ultrasound probe. The system further includes a housing supported by a base. The housing includes a connector port and a cable manage passage. The cable manage passage positioned at an upper end of the housing distal to the base. The cable extending through the cable manage passage, and is attached to the connector port. The ultrasound probe holder is coupled to a front side of the housing.

Optionally, the cable manage passage may extend along two orthogonal directions of the housing.

Optionally, the system includes a display such that the ultrasound probe holder is interposed between the housing and the display. Additionally or alternatively, the system includes an arm mount. The display may be coupled to the arm mount. The arm mount may be configured to adjust at least one of a rotational position, a tilt angle, or a vertical position of the display with respect to the housing. Additionally or alternatively, the system further includes a vertical track extending along the front side of the housing. The arm mount may be configured to traverse along the vertical track. Additionally or alternatively, a length of the vertical track may be based on a length of the cable. Additionally or alternatively, the arm mount may be configured to guide the cable between the housing and the display.

Optionally, the housing may include a first vent proximate to the cable manage passage configured to regulate a temperature within the housing. Additionally or alternatively, the housing may include a second vent positioned proximate to the base. The first and second vents may be configured to generate a stack effect within the housing.

Optionally, the housing may include a channel extending within the housing. The channel may have a first and second vent positioned at opposing ends.

Optionally, the housing may be configured to maintain a position of the cable within a footprint defined by the housing.

Optionally, the connector port may be positioned along a back side of the housing.

Optionally, the connector port may be positioned between the cable manage passage and a mid-point of the housing.

Optionally, the base may include a plurality of wheels.

Optionally, the cable manage passage may include a first entry aperture and a second entry aperture positioned at opposing lateral sides of the housing.

Optionally, the cable manage passage may include an exiting aperture positioned at a back side of the housing.

Optionally, a position of the cable manage passage is based on a length of the cable.

In an embodiment a housing is provided an ultrasound imaging system. The housing includes an arm mount coupled to a front side of the housing. The arm mount is configured to traverse along a vertical track of the housing. The arm mount is further configured to adjust at least one of a rotational position, a tilt angle, or a vertical position of a display. The housing includes a connector port coupled to a back side of the housing. The housing further includes a base and a cable manage passage positioned at opposing ends of the housing. The cable manage passage extending along two orthogonal directions of the housing. The cable manage passage including an entry aperture along a first orthogonal direction, and an exiting aperture along a second orthogonal direction. The connector port is positioned proximate to the exiting aperture.

Optionally, the connector port may be attached to a cable of an ultrasound probe. A height of the cable manage passage may be based on a length of the cable.

In an embodiment a method (e.g., for manufacturing a housing for an ultrasound imaging system) is provided. The method includes providing a cover segment and a base. The cover segment includes a cable manage passage extending along two orthogonal directions. The cable manage passage includes an entry aperture along a first orthogonal direction and an exiting aperture along a second orthogonal direction. The method further includes defining a distance between the cover segment and the base based on a length of a cable of an ultrasound probe.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An ultrasound imaging system comprising:
   an ultrasound probe including a cable;

a housing including a connector port, wherein the connector port is configured to attach the ultrasound probe to the housing;

a display coupled to the housing via an arm mount; and a probe holder comprising a plurality of slots that are linearly arranged along a length of the probe holder, the probe holder positioned along an uppermost edge of the display and higher than an entirety of the housing when the arm mount is in a fully raised position, wherein at least one of the plurality of slots of the probe holder is configured to hold the ultrasound probe, and wherein, when positioned in the probe holder, the cable of the ultrasound probe is configured to hang freely from the probe holder without touching the ground, wherein the probe holder is directly connected to the uppermost edge of the display.

2. The ultrasound imaging system of claim 1, further comprising a base, wherein the base is configured to be in contact with the ground and to support the housing.

3. The ultrasound imaging system of claim 2, wherein the base comprises a plurality of wheels configured to be in contact with the ground, wherein the plurality of wheels enables the ultrasound imaging system to be mobile.

4. The ultrasound imaging system of claim 2, wherein when positioned in the probe holder, the cable of the ultrasound probe is configured to hang freely from the probe holder while not extending lower than the base.

5. The ultrasound imaging system of claim 1, wherein the arm mount is configured to traverse along a vertical track of the housing in order to adjust a vertical position of the display with respect to the housing.

6. The ultrasound imaging system of claim 5, wherein the display is configured to be moved between a first vertical position and a second vertical position, wherein the second vertical position is lower than the first vertical position, wherein the probe holder is configured to move concurrently with the display between the first vertical position and the second vertical position, and, wherein, when positioned in the probe holder, the cable of the ultrasound probe is configured to hang freely above the ground with the display in either the first vertical position or the second vertical position.

7. The ultrasound imaging system of claim 5, wherein a length of the vertical track is based on a length of the cable to prevent the cable from being in contact with the ground when the probe is positioned in the probe holder.

8. The ultrasound imaging system of claim 1, wherein the arm mount includes at least one of a fastener configured to hold at least a portion of the cable to the arm mount and a channel configured to hold at least a portion of the cable to the arm mount.

9. The ultrasound imaging system of claim 1, wherein when positioned in the probe holder, the cable of the ultrasound probe is configured to hang freely from the probe holder while not extending lower than the housing.

10. The ultrasound imaging system of claim 1, wherein the cable hangs freely between the display and a front side of the housing.

11. The ultrasound imaging system of claim 10, wherein a portion of the cable hangs freely down toward the ground beneath the uppermost edge.

12. The ultrasound imaging system of claim 1, wherein the housing comprises a front side and a back side opposite the front side, wherein the arm mount is attached to the front side of the housing, wherein the housing is configured to at least partially define a cable manage passage configured to guide at least one cable from the front side of the housing to the connector port.

13. The ultrasound imaging system of claim 12, wherein the connector port is on the back side of the housing.

14. The ultrasound imaging system of claim 12, wherein the housing comprises a cover segment and wherein the cable manage passage is defined by an upper portion of the housing and the cover segment.

15. The ultrasound imaging system of claim 1, wherein the housing is configured to maintain the ultrasound probe, including the cable, within a footprint of the ultrasound imaging system.

16. The ultrasound imaging system of claim 15, wherein the footprint of the ultrasound imaging system is defined by a plurality of distal edges of the ultrasound imaging system.

17. The ultrasound imaging system of claim 15, wherein the ultrasound imaging system further comprises a base including a plurality of wheels, and wherein the footprint is defined by a distal edge of the display and a plurality of distal edges of the plurality of wheels.

18. The ultrasound imaging system of claim 1, wherein all of the uppermost edge of the display is in contact with the probe holder.

19. The ultrasound imaging system of claim 1, wherein the probe holder is substantially the same width as the display in a direction along the uppermost edge.

20. The ultrasound imaging system of claim 1, wherein the probe holder is permanently fixed in a position adjacent to the display.

21. An ultrasound imaging system comprising:
an ultrasound probe including a cable;
a housing including a connector port, wherein the connector port is configured to attach the ultrasound probe to the housing;
a display coupled to the housing via an arm mount; and
a probe holder comprising a plurality of slots that are linearly arranged along a length of the probe holder, wherein at least one of the plurality of slots of the probe holder is configured to hold the ultrasound probe, and wherein, when positioned in the probe holder, the cable of the ultrasound probe is configured to hang freely from the probe holder without touching the ground, wherein the probe holder is positioned along a top edge of the display,
wherein the probe holder is directly connected to the top edge of the display.

22. An ultrasound imaging system comprising:
an ultrasound probe including a cable;
a housing including a connector port, wherein the connector port is configured to attach the ultrasound probe to the housing;
a display coupled to the housing via an arm mount; and
a probe holder comprising a plurality of slots that are linearly arranged along a length of the probe holder, the probe holder positioned along an uppermost edge of the display and higher than an entirety of the housing when the arm mount is in a fully raised position, wherein at least one of the plurality of slots of the probe holder is configured to hold the ultrasound probe, and wherein, when the probe is positioned in the probe holder, the cable of the ultrasound probe is configured to hang freely from the probe holder without touching the ground,
wherein the probe holder is substantially the same width as the display in a direction along the uppermost edge of the display, and wherein the probe holder is directly connected to the uppermost edge of the display.

\* \* \* \* \*